United States Patent
Heidemann et al.

(10) Patent No.: US 9,409,154 B2
(45) Date of Patent: Aug. 9, 2016

(54) PROCESS FOR PRODUCING SN-COMPRISING CATALYSTS

(71) Applicant: BASF SE, Ludwigshafen (DE)

(72) Inventors: Thomas Heidemann, Viernheim (DE); Petr Kubanek, Mannheim (DE); Joana C. Tsou, Brüssel (BE); Heiko Baas, Meckenheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 14/691,663

(22) Filed: Apr. 21, 2015

(65) Prior Publication Data

US 2015/0224480 A1    Aug. 13, 2015

Related U.S. Application Data

(62) Division of application No. 13/679,107, filed on Nov. 16, 2012.

(60) Provisional application No. 61/560,830, filed on Nov. 17, 2011.

(51) Int. Cl.

| | |
|---|---|
| *B01J 23/835* | (2006.01) |
| *B01J 23/14* | (2006.01) |
| *C07D 295/00* | (2006.01) |
| *C07C 213/02* | (2006.01) |
| *B01J 37/03* | (2006.01) |
| *B01J 37/06* | (2006.01) |
| *B01J 37/08* | (2006.01) |
| *B01J 37/12* | (2006.01) |
| *B01J 37/16* | (2006.01) |
| *B01J 35/10* | (2006.01) |
| *B01J 21/04* | (2006.01) |
| *B01J 35/00* | (2006.01) |
| *B01J 37/02* | (2006.01) |
| *B01J 37/18* | (2006.01) |
| *B01J 23/889* | (2006.01) |
| *B01J 23/78* | (2006.01) |
| *B01J 23/83* | (2006.01) |
| *B01J 23/847* | (2006.01) |
| *B01J 23/888* | (2006.01) |
| *B01J 33/00* | (2006.01) |

(52) U.S. Cl.
CPC ............... *B01J 23/835* (2013.01); *B01J 21/04* (2013.01); *B01J 23/14* (2013.01); *B01J 35/0006* (2013.01); *B01J 35/1014* (2013.01); *B01J 35/1019* (2013.01); *B01J 37/03* (2013.01); *B01J 37/031* (2013.01); *B01J 37/035* (2013.01); *B01J 37/06* (2013.01); *B01J 37/08* (2013.01); *B01J 37/086* (2013.01); *B01J 37/12* (2013.01); *B01J 37/16* (2013.01); *C07C 213/02* (2013.01); *C07D 295/00* (2013.01); *B01J 23/78* (2013.01); *B01J 23/83* (2013.01); *B01J 23/847* (2013.01); *B01J 23/888* (2013.01); *B01J 23/8892* (2013.01); *B01J 33/00* (2013.01); *B01J 37/0203* (2013.01); *B01J 37/18* (2013.01); *B01J 2523/00* (2013.01); *Y02P 20/582* (2015.11)

(58) Field of Classification Search
CPC ...... B01J 23/855; B01J 23/14; B01J 35/1014; B01J 35/1019; B01J 37/06; B01J 37/031; B01J 37/12; B01J 37/16; B01J 37/0203; B01J 37/086
USPC .......... 502/325, 332, 335, 337, 345, 349, 355
See application file for complete search history.

(56) References Cited

U.S. PATENT DOCUMENTS

| | | |
|---|---|---|
| 2003/0089591 A1 | 5/2003 | Wolfert et al. |
| 2005/0000791 A1 | 1/2005 | Wolfert et al. |
| 2011/0137030 A1 | 6/2011 | Kubanek et al. |

FOREIGN PATENT DOCUMENTS

| | | |
|---|---|---|
| CN | 1528671 A | 9/2004 |
| CN | 101612594 A | 12/2009 |
| EP | 0224947 A1 | 6/1987 |
| EP | 1 312 599 A1 | 5/2003 |
| EP | 1 312 600 A1 | 5/2003 |
| WO | WO-2006078240 A1 | 7/2006 |
| WO | PCT/EP2010/068375 | 11/2010 |
| WO | PCT/EP2010/068376 | 11/2010 |
| WO | PCT/EP2010/069637 | 12/2010 |
| WO | WO-2011067199 A1 | 6/2011 |
| WO | WO-2011094713 A1 | 8/2011 |
| WO | PCT/EP2011/065608 | 9/2011 |
| WO | PCT/EP2011/071707 | 12/2011 |

OTHER PUBLICATIONS

U.S. Appl. No. 12/958,597, filed Dec. 2, 2010, Kubanek, Petr.
U.S. Appl. No. 12/958,545, filed Dec. 2, 2010, Kubanek, Petr.
U.S. Appl. No. 13/183,683, filed Jul. 15, 2011, Königsmann, Lucia.
U.S. Appl. No. 13/468,689, filed Jul. 20, 2011, Schneider, Christian.
U.S. Appl. No. 13/311,371, filed Dec. 5, 2011, Haase, Stefanie.
Deacon, Paul R., et al., "Synthesis and Characterisation of Tin(II) and Tin(IV) Citrates", J. Chem. Soc., Dalton Trans., (1997), pp. 3705-3712.
Smith, T.D., et al., "Chelates Formed by Tin(II) with Citric and Tartaric Acids, and their Interaction with Certain Transition-Metal Ions", J. Chem. Soc., (1965), pp. 2145-2149.
Ullmann's Encyclopedia of Industrial Chemistry, "Fixed Bed Reactors", 5th Ed., vol. B4, (1992), pp. 199-238.

*Primary Examiner* — Anthony J Zimmer
(74) *Attorney, Agent, or Firm* — Drinker Biddle & Reath LLP

(57) ABSTRACT

The present invention relates to a process for producing a supported tin-comprising catalyst, wherein a solution (S) comprising tin nitrate and at least one complexing agent is applied to the support, where the solution (S) does not comprise any solid or has a solids content of not more than 0.5% by weight based on the total amount of dissolved components.

8 Claims, No Drawings

PROCESS FOR PRODUCING SN-COMPRISING CATALYSTS

This application is a divisional of Ser. No. 13/679,107, filed Nov. 16, 2012, which claims benefit to US provisional application Ser. No. U.S. 61/560,830 filed on Nov. 17, 2011, both of which are incorporated herein by reference in their entirety for all their useful purposes.

The present invention relates to a process for producing a supported tin-comprising (Sn-comprising) catalyst using a solution (S) comprising tin nitrate and at least one complexing agent, where the solution (S) does not comprise any solid or has only a very low solids content. Furthermore, the present invention relates to the supported tin-comprising catalyst as such and also to the use of this supported tin-comprising catalyst in a process for preparing amines.

WO 2011/067199 relates to catalysts comprising aluminum oxide, tin, copper, nickel and cobalt and a process for preparing an amine by reacting a primary or secondary alcohol, aldehyde and/or ketone with hydrogen and a nitrogen compound selected from the group consisting of ammonia, primary and secondary amines in the presence of this catalyst comprising aluminum oxide, tin, copper, nickel and cobalt.

The metal components comprised in the catalysts of WO 2011/067199, in particular tin (Sn), copper (Cu), cobalt (Co), nickel (Ni), are, in the production of the catalyst, firstly used in salt form and applied by means of a precipitation process to the catalyst support (preferably aluminum oxide) in the process of WO 2011/067199. While nickel, cobalt and copper can be used in the form of their nitrates, tin is used only in the form of tin chloride. The use of tin nitrate is not disclosed in WO 2011/067199 for production of the catalyst and is also not possible under the catalyst production conditions described there because tin nitrate solutions are metastable and tin very quickly begins to precipitate from such solutions. However, the tin chloride solutions described for production of the catalyst in WO 2011/067199 have the disadvantage that the chloride or the chlorine formed therefrom during or after precipitation of the tin is highly corrosive even in traces, which leads to corrosion problems in the process for producing the catalyst and also in the later use of the catalyst. For example, pit corrosion can occur.

It is known in the scientific literature that tin can also form complexes by reaction of tin chloride with citric acid or tartronic acid. Thus, for example, P. R. Deacon et al., J. Chem. Soc. Dalton Trans. 1997, pages 3705 to 3712, and T. D. Smith, J. Chem. Soc. 1965, pages 2145 to 2149, describe the preparation of such tin complexes and their spectroscopic characterization. However, the use of tin nitrate in the preparation of the tin complexes and their use for producing catalysts or the use of such catalysts for preparing amines is disclosed nowhere in these documents.

It is an object of the present invention to provide a new process for producing tin-comprising catalysts and/or the tin-comprising catalysts as such.

The object is achieved by the process of the invention for producing a supported tin-comprising catalyst, wherein a solution (S) comprising tin nitrate and at least one complexing agent is applied to the support, where the solution (S) does not comprise any solid or has a solids content of not more than 0.5% by weight based on the total amount of dissolved components.

The process of the invention enables tin as metal component to be introduced into a catalyst or applied to the catalyst support in a simple and advantageous way. The tin nitrate solutions with complexing agent which are used have a high stability which is maintained over a very long period of time. The stability is shown by these solutions (S) remaining clear and no or only very little precipitate and/or turbidity in the form of precipitated tin being formed. The solution (S) thus does not comprise any solid or comprises only very small amounts of solid.

Owing to the addition of at least one complexing agent to the solution (S) comprising tin nitrate, it is also ensured that the tin nitrate solution is stable at room temperature or higher temperatures. Tin nitrate solutions without complexing agents are metastable or unstable at room temperature or higher temperatures since they quickly become turbid due to precipitating tin. The stability of tin nitrate solutions without complexing agents, in particular aqueous tin nitrate solutions, can otherwise be increased only when these solutions are produced at very low temperatures, generally less than 0° C. or preferably less than −10° C. Although more stable tin nitrate solutions can be produced in this way, it is technically very complicated to use strongly cooled tin nitrate solutions without complexing agents because the further catalyst production steps are associated with higher temperatures. The addition of at least one complexing agent enables stable tin nitrate solutions to be stored in an advantageous way for some days to a number of weeks and used for catalyst production under industrially relevant conditions, i.e. at room temperature and above.

In catalysts produced in this way, the tin used is stably and completely bound to the catalyst support. In addition, the catalysts of the invention are more selective than catalysts which comprise halogen (in particular chlorine) and/or for which a metastable tin nitrate solution (without complexing agent) is used. This selectivity gain is of critical importance especially in industrial processes/plants because these even relatively small selectivity increases produce great cost advantages.

Premature precipitation of tin due to lack of cooling or lack of addition of complexing agent from conventional tin nitrate solutions before further processing for catalyst production has an adverse effect on the performance of the later catalyst. Presumably, the dispersion of the tin or the interaction with any other active components which may be present in the later catalyst is adversely affected when the tin nitrate is not provided in the form of a stable solution.

As a result of the use of tin nitrate instead of tin chloride, there are also no corrosion problems in catalyst production or in the use of these catalysts for preparing amines due to residual chloride or chlorine remaining in the catalyst. Thus, in particular, the occurrence of pit corrosion in the plants used can be suppressed.

The present invention is described in more detail below.

The solution (S) used for producing the supported tin-comprising catalyst comprises tin nitrate and at least one complexing agent. The solution (S) does not comprise any solid or has a solids content of not more than 0.5% by weight based on the total amount of dissolved components. If the solution (S) has a solids content, this is preferably not more than 0.1% by weight, in particular not more than 0.01% by weight, based on the total amount of dissolved components. As indicated above, the solution (S) is a stable, in particular clear, tin nitrate solution because it does not comprise any solid or has only a very low solids content. The solid, if present, generally comprises one or more of the components comprised in the solution (S), e.g. precipitated tin nitrate, possibly further precipitated salts or the precipitated complexing agent and mixtures thereof or reaction products of the individual components.

The solution (S) is preferably stable (clear) for a period of from at least one day up to 30 days after production of the corresponding solution; in particular, the time frame is from at least five days up to 15 days. Furthermore, the solution (S) is preferably stable (clear) in a temperature range from −20° C. up to 120° C., preferably from 10° C. to 70° C., particularly preferably at room temperature (from 20 to 25° C.).

As solvent for the solution (S), it is possible in principle to use any solvent known to those skilled in the art which is suitable for dissolving salts, in particular tin nitrate, and/or complexing agents. The solution (S) is preferably an aqueous solution.

Tin nitrate as such is known to those skilled in the art. Tin nitrate is preferably prepared in situ by dissolving alkaline tin (tin granules) in nitric acid. Preference is also given to the tin nitrate being prepared at low temperatures, preferably <0° C., particularly preferably <−10° C. Particular preference is given to producing an aqueous tin nitrate solution in which the water content is adjusted by addition of ice, cooled water and/or dilute nitric acid.

As complexing agent, it is in principle possible to use any complexing agent known to those skilled in the art which can form a complex with tin, preferably in the oxidation state +2. Optionally, two or more different complexing agents can be used. Preferred complexing agents are selected from among at least bidentate hydroxycarboxylic acids, dicarboxylic acids, multicarboxylic acids, aminocarboxylic acids and salts of the abovementioned acids.

The complexing agent is more preferably selected from among glycolic acid, lactic acid, hydracylic acid, hydroxybutyric acid, hydroxyvaleric acid, malic acid, mandelic acid, citric acid, sugar acids, tartronic acid, tartaric acid, oxalic acid, malonic acid, maleic acid, succinic acid, glutaric acid, adipic acid, glycine, hippuric acid, EDTA (ethylenediaminetetraacetic acid), alanine, valine, leucine and isoleucine.

The complexing agent is particularly preferably citric acid.

In addition, the solution (S) can comprise further components. These further components are preferably metal salts whose metal component is likewise to be introduced into the supported tin-comprising catalyst. Preference is given to at least one metal salt being selected from among a nickel salt, a cobalt salt and a copper salt. Further salts may optionally also be used, for example rhenium salts, ruthenium salts, iron salts or zinc salts. Furthermore, preference is given to the metal salt and/or the solution (S) not comprising any halide, in particular no chloride. Greater preference is given to the corresponding nitrates of the abovementioned metal salts being used as further metal salts. The further metal salt is particularly preferably a metal salt selected from among nickel nitrate, cobalt nitrate and copper nitrate.

In the solution (S), the individual components can be present in any ratios relative to one another. Tin nitrate and the further metal salts optionally present are preferably present in proportions of from 1 to 50% by weight, preferably from 5 to 20% by weight, in the solution (S), in particular in water (the percentages by weight are based on the sum of all salts relative to the total weight of the solution (S)). The molar ratio of complexing agent to tin in the solution (S) is preferably at least 1.5:1, particularly preferably 2:1 (tin is in this case present as tin nitrate). In particular, the molar ratio of citric acid to tin is 2:1.

In a preferred embodiment of the present invention, the solution (S) comprises tin nitrate, nickel nitrate, cobalt nitrate, copper nitrate and citric acid.

The solution (S) can be produced by methods known to those skilled in the art, for example by successive addition of the individual components, premixing of at least two components or by simultaneous mixing of all components. The solution (S) is preferably produced by i) dissolving tin in nitric acid at a temperature of not more than 5° C. and subsequently adding at least one complexing agent, or ii) by dissolving at least one complexing agent in nitric acid at a temperature of from 0° C. to 50° C., preferably at room temperature, and subsequently adding tin.

According to the invention, the supported tin-comprising catalyst is produced by applying the above-described solution (S) to the catalyst support by methods known to those skilled in the art. The catalyst support can optionally already comprise one or more metal-active components. Possible supports (support materials) are in principle all supports known to those skilled in the art. The support is preferably aluminum oxide. Mixtures of aluminum oxide and other support materials can optionally also be used, for example silicon-comprising and/or zirconium-comprising supports. Further suitable supports, processes for applying salt-comprising solutions and also further process steps for producing a supported catalyst as such are disclosed, for example, in WO 2011/067199.

The application of the solution (S) to the catalyst support is preferably carried out by a precipitation process as described, for example, in WO 2011/067199. In this precipitation process, the tin nitrate, at least one complexing agent and optionally at least one further metal salt are precipitated from the solution (S) onto the support by addition of at least one base (B).

The base (B) is preferably added as aqueous solution. The base (B) is preferably selected from among sodium carbonate, sodium hydroxide, potassium carbonate, potassium hydroxide and bases which are free of alkali metals, for example ammonia, ammonium carbonate, ammonium hydrogencarbonate, ammonium carbamate, ammonium oxalate, ammonium malonate, urotropin or urea, with preference being given to the base (B) being sodium carbonate.

For example, the catalysts according to the invention can be produced in the process of the invention by joint precipitation (coprecipitation) of all their components. For this purpose, an aqueous salt solution comprising the catalyst components is advantageously admixed hot while stirring with an aqueous base, for example sodium carbonate, sodium hydroxide, potassium carbonate or potassium hydroxide, until the precipitation is complete. Bases free of alkali metals, e.g. ammonia, ammonium carbonate, ammonium hydrogencarbonate, ammonium carbamate, ammonium oxalate, ammonium malonate, urotropin, urea, etc., can also be employed. The type of salts used is generally not critical: since the water-solubility of the salts is the main factor of importance in this procedure, a criterion is the salts having the good water-solubility required for producing these relatively highly concentrated salt solutions. It is considered to be self evident that, when selecting the salts of the individual components, naturally only salts having anions which do not lead to interference, whether by causing undesirable precipitation or by making the precipitation difficult or impossible due to complex formation, are chosen.

The precipitates obtained in these precipitation reactions are generally chemically nonuniform and comprise, inter alia, mixtures of the oxides, oxide hydrates, hydroxides, carbonates and insoluble and basic salts of the metals used. To aid the filterability of the precipitates, it can be advantageous for them to be aged, i.e. for them to be left to stand for some time after precipitation, optionally hot or with air being passed through.

The precipitates obtained by these precipitation processes can be processed further in the usual way. Firstly, the precipitates are washed. The content of alkali metal which has been introduced via any (mineral) base used as precipitant can be influenced by the duration of washing and the temperature and amount of washing water. In general, the content of alkali metal will be decreased by increasing the washing time or raising the temperature of the washing water. After washing, the precipitated material is generally dried at from 80 to 200° C., preferably from 100 to 150° C., and then calcined. The calcination (calcination step) is generally carried out at temperatures in the range from 300 to 800° C., preferably from 400 to 600° C., in particular from 420 to 550° C.

Furthermore, preference is given to the application of the solution (S) to the support being followed by at least one further step selected from among a drying step, a calcination step, a conditioning step, a shaping step, a reduction step and a passivation step.

The specific way in which the above-described further steps are carried out is disclosed, for example, in WO 2011/067199. Specific temperature ranges for the drying step and for the calcination step are also indicated in the above text in the context of the precipitation process described by way of example.

In a preferred embodiment of the present invention, the complexing agent is removed from the supported tin-comprising catalyst during or after the calcination step. This is particularly preferably achieved by the complexing agent being removed from the supported, tin-comprising catalyst by oxidative combustion during the calcination step. The complexing agent is preferably removed from the catalyst without leaving a residue (completely) in the calcination step.

The present invention further provides a supported tin-comprising catalyst as such which can be produced by the above-described process.

The supported tin-comprising catalyst of the invention preferably comprises from 0.2 to 5% by weight of tin, calculated as SnO. Preference is also given to the catalyst of the invention comprising at least one additional metal component selected from among copper, nickel and cobalt. Preference is likewise given to the catalyst support being aluminum oxide.

The catalysts of the invention are preferably used in the form of catalysts which consist of only catalytically active composition and optionally a shaping aid (e.g. graphite or stearic acid), if the catalyst is used as shaped body, i.e. do not comprise any further catalytically active accompanying materials. In this context, the oxidic support material, preferably aluminum oxide ($Al_2O_3$), is counted as part of the catalytically active composition.

In the use of the catalysts, the catalytically active composition which has been milled to a powder is introduced into the reaction vessel or the catalytically active composition is milled, mixed with shaping aids, shaped and heat treated and arranged as shaped catalyst bodies, for example as pellets, spheres, rings, extrudates (e.g. rods), in the reactor.

The indicated concentrations (in % by weight) of the components of the catalyst in each case relate, unless indicated otherwise, to the catalytically active composition of the finished catalyst after the last heat treatment and before reduction with hydrogen.

The catalytically active composition of the catalyst after the last heat treatment and before reduction with hydrogen is defined as the sum of the masses of the catalytically active constituents and the abovementioned catalyst support materials and comprises essentially the following constituents: aluminum oxide ($Al_2O_3$), oxygen-comprising compounds of tin and optionally oxygen-comprising compounds of copper, nickel and/or cobalt.

The sum of the abovementioned constituents of the catalytically active composition is usually from 70 to 100% by weight, preferably from 80 to 100% by weight, more preferably from 90 to 100% by weight, even more preferably from >95% by weight to 100% by weight, particularly preferably from >98% by weight to 100% by weight, in particular from >99% by weight to 100% by weight, e.g. precisely 100% by weight.

The catalytically active composition of the catalysts of the invention and those used in the process of the invention can further comprise one or more elements (oxidation state 0) or inorganic or organic compounds thereof selected from groups I A to VI A and I B to VII B and VIII of the Periodic Table.

Examples of such elements and compounds thereof are: transition metals such as Mn and $MnO_2$, W and tungsten oxides, Ta and tantalum oxides, Nb and niobium oxides or niobium oxalate, V and vanadium oxides or vanadyl pyrophosphate; lanthanides such as Ce and $CeO_2$ or Pr and $Pr_2O_3$; alkaline earth metal oxides such as SrO; alkaline earth metal carbonates such as $MgCO_3$, $CaCO_3$ and $BaCO_3$; boron oxide ($B_2O_3$).

The catalytically active composition of the catalyst preferably comprises, before reduction with hydrogen, from 0.2 to 5.0% by weight, in particular from 0.4 to 4.0% by weight, more particularly from 0.6 to 3.0% by weight, more particularly preferably from 0.7 to 2.5% by weight, of oxygen-comprising compounds of tin, calculated as SnO.

The catalytically active composition of the catalyst optionally comprises, before reduction with hydrogen, preferably from 5.0 to 35% by weight, in particular from 10 to 30% by weight, more particularly from 12 to 28% by weight, very particularly preferably from 15 to 25% by weight, of oxygen-comprising compounds of cobalt, calculated as CoO.

The catalytically active composition of the catalyst optionally further comprises, in one embodiment of the present invention, before reduction with hydrogen, preferably from 15 to 80% by weight, in particular from 30 to 70% by weight, more particularly from 35 to 65% by weight, of oxygen-comprising compounds of aluminum, calculated as $Al_2O_3$, from 1 to 20% by weight, in particular from 2 to 18% by weight, more particularly from 5 to 15% by weight, of oxygen-comprising compounds of copper, calculated as CuO, and from 5 to 35% by weight, in particular from 10 to 30% by weight, more particularly from 12 to 28% by weight, very particularly preferably from 15 to 25% by weight, of oxygen-comprising compounds of nickel, calculated as NiO.

If present, the molar ratio of nickel to copper is preferably greater than 1, particularly preferably greater than 1.2, more particularly preferably in the range from 1.8 to 8.5.

The BET surface area (ISO 9277:1995) of the catalyst of the invention and those used in the process of the invention is preferably in the range from 30 to 250 $m^2/g$, in particular in the range from 90 to 200 $m^2/g$, more particularly in the range from 130 to 190 $m^2/g$. These ranges are achieved, in particular, by means of calcination temperatures in the range from 400 to 600° C., in particular from 420 to 550° C., in the production of the catalyst.

In a preferred embodiment of the present invention, the catalyst of the invention comprises
  i) from 0.2 to 5% by weight of tin,
  ii) from 15 to 80% by weight of aluminum,
  iii) from 1 to 20% by weight of copper,
  iv) from 5 to 35% by weight of nickel and
  v) from 5 to 35% by weight of cobalt,
  where the proportions by weight of the components i) to v) are determined as oxides after a calcination step and before a reduction step using hydrogen.

In a further preferred embodiment of the present invention, the catalyst of the invention does not comprise any halogen (for example in the form of halide), in particular no chlorine (for example in the form of chlorides or other chlorine-comprising compounds).

The present invention further provides a process for preparing an amine (A) in the presence of a catalyst according to the invention as set forth above. Processes for preparing amines are known in principle to those skilled in the art. In the following text, the general process conditions such as pressure, temperature, ratios of starting materials, etc., will firstly be described. The specific starting materials which can be used, e.g. a primary alcohol or a nitrogen-comprising compound (N), and the product obtained in the process of the invention (amine (A)) will subsequently be described. The nitrogen-comprising compound (N) used as starting material can also be referred to as aminating agent or amine component. For the purposes of the present invention, amination is the reaction of such a nitrogen-comprising compound (N) with a further starting material such as a primary alcohol or an aldehyde to form the amine (A).

The process of the invention for preparing the amine (A) can be carried out continuously or batchwise. It is preferably carried out continuously.

For the synthesis in the gas phase, the starting materials are vaporized in a targeted manner, preferably in a recycle gas stream, and introduced in gaseous form into the reactor. Suitable amines for a gas-phase synthesis are amines which, owing to their boiling points and the boiling points of the starting materials from which they are derived, can be kept in the gas phase within the process parameters employed. The recycle gas serves firstly to vaporize the starting materials and secondly as reactant for the amination.

In the recycle gas procedure, the starting materials (alcohol, aldehyde and/or ketone, hydrogen and the nitrogen compound) are vaporized in a recycle gas stream and introduced in gaseous form into the reactor.

The starting materials (alcohol, aldehyde and/or ketone, hydrogen and the nitrogen compound) can also be vaporized as aqueous solutions and fed together with the recycle gas stream to the catalyst bed.

Preferred reactors are tube reactors. Examples of such reactors using a recycle gas stream may be found in Ullmann's Encyclopedia of Industrial Chemistry, 5th Ed., Vol. B 4, pages 199-238, "Fixed-Bed Reactors".

As an alternative, the reaction is advantageously carried out in a cell-and-tube reactor or in a single-stream plant.

In a single-stream plant, the tube reactor in which the reaction is carried out can comprise a series arrangement of a plurality of (e.g. two or three) individual tube reactors. Intermediate introduction of feed (comprising the starting material and/or ammonia and/or $H_2$) and/or recycle gas and/or reactor output from a downstream reactor is optionally advantageous here.

The amount of recycle gas is preferably in the range from 40 to 1500 m³ (at operating pressure)/[m³ of catalyst (bed volume)·h], in particular in the range from 100 to 700 m³ (at operating pressure)/[m³ of catalyst (bed volume)·h].

The recycle gas preferably comprises at least 10% by volume, in particular from 50 to 100% by volume, very particularly preferably from 80 to 100% by volume, of $H_2$.

All starting materials and products which are not easily vaporized or are thermally labile are suitable for the synthesis in the liquid phase. In these cases, a further advantage is that vaporization and recondensation of the amine in the process can be dispensed with.

The process of the invention for preparing an amine (A) is preferably carried out continuously, with the above-described catalyst preferably being arranged as a fixed bed in the reactor. Flow into the fixed catalyst bed can be either from above or from below. The gas flow is set by means of temperature, pressure and amount so that relatively high-boiling reaction products also remain in the gas phase.

The nitrogen-comprising compound (N) can be used in stoichiometric, substoichiometric or superstoichiometric amounts relative to the compound which has at least one alcoholic hydroxyl group or aldehyde group or keto group and is to be aminated.

In the case of amination of alcohols, aldehydes or ketones by means of primary or secondary amines, the amine is preferably used in an approximately stoichiometric amount or slightly superstoichiometric amount per mole of alcoholic hydroxyl group, aldehyde group or keto group to be aminated.

The amine component (nitrogen-comprising compound (N)) is preferably used in from 0.90 to 100 times the molar amount, in particular in from 1.0 to 10 times the molar amount, in each case based on the alcohol, aldehyde and/or ketone used.

Ammonia in particular (as nitrogen-comprising compound (N)) is generally used in a 1.5- to 250-fold, preferably 2- to 100-fold, in particular 2- to 10-fold, molar excess per mole of alcoholic hydroxyl group, aldehyde group or keto group to be reacted.

Larger excesses both of ammonia and of primary or secondary amines are possible.

The process is preferably operated with an outward gas flow of from 5 to 800 standard cubic meters/h, in particular from 20 to 300 standard cubic meters/h. (Standard cubic meters=volume converted to standard conditions).

The amination of the primary or secondary alcohol groups, aldehyde groups or keto groups of the starting material can be carried out in the liquid phase or in the gas phase.

When working in the liquid phase, the starting materials (alcohol, aldehyde or ketone plus ammonia or amine) are simultaneously conveyed in the liquid phase at pressures of generally from 5 to 30 MPa (50-300 bar), preferably from 5 to 25 MPa, particularly preferably from 15 to 25 MPa, and temperatures of generally from 80 to 350° C., in particular from 100 to 300° C., preferably from 120 to 270° C., particularly preferably from 130 to 250° C., in particular from 170 to 230° C., including hydrogen, over the catalyst which is usually present in a fixed bed reactor which is preferably heated from the outside. Both a downflow mode and an upflow mode are possible. The space velocity over the catalyst is generally in the range from 0.05 to 5 kg, preferably from 0.1 to 2 kg, particularly preferably from 0.2 to 0.6 kg, of alcohol, aldehyde or ketone per liter of catalyst (bed volume) and hour. The starting materials can optionally be diluted with a suitable solvent such as tetrahydrofuran, dioxane, N-methylpyrrolidone or ethylene glycol dimethyl ether. It is advantageous to heat the reactants before being fed into the reaction vessel, preferably to the reaction temperature.

When working in the gas phase, the gaseous starting materials (alcohol, aldehyde or ketone plus ammonia or amine) are passed in a gas stream sufficiently large to effect vaporization, preferably hydrogen, at pressures of generally from 0.1 to 40 MPa (from 1 to 400 bar), preferably from 0.1 to 10 MPa, particularly preferably from 0.1 to 5 MPa, in the presence of hydrogen over the catalyst. The temperatures for the amination of alcohols are generally from 80 to 350° C., in particular from 100 to 300° C., preferably from 120 to 270° C., particularly preferably from 160 to 250° C. The reaction temperatures in the hydrogenative amination of aldehydes and ketones are generally from 80 to 350° C., in particular from 90 to 300° C., preferably from 100 to 250° C. Flow into the fixed catalyst bed can be either from above or from below. The required gas stream is preferably obtained by means of a recycle gas mode of operation.

The space velocity over the catalyst is generally in the range from 0.01 to 2 kg, preferably from 0.05 to 0.5 kg, of alcohol, aldehyde or ketone per liter of catalyst (bed volume) and hour.

The hydrogen is generally fed to the reaction in an amount of from 5 to 400 l, preferably in an amount of from 50 to 200 l, per mole of alcohol, aldehyde or ketone component, with the liter figures in each case having been converted to standard conditions (S.T.P.).

The amination of aldehydes and ketones differs from the amination of alcohols in that at least stoichiometric amounts of hydrogen have to be present in the amination of aldehydes and ketones.

Both when working in the liquid phase and when working in the gas phase, the use of relatively high temperatures and relatively high total pressures and space velocities over the catalyst is possible. The pressure in the reaction vessel, which is the sum of the partial pressures of the aminating agent, of the alcohol, aldehyde or ketone and of the reaction products formed and also of any solvent concomitantly used at the indicated temperatures, is advantageously increased to the desired reaction pressure by injection of hydrogen.

Both when working continuously in the liquid phase and when working continuously in the gas phase, the excess aminating agent can be circulated together with the hydrogen.

If the catalyst is arranged as a fixed bed, it can be advantageous in respect of the selectivity of the reaction for the shaped catalyst bodies in the reactor to be mixed with inert packing elements to "dilute" them, so to speak. The proportion of the packing elements in such catalyst preparations can be from 20 to 80 parts by volume, preferably from 30 to 60 parts by volume and particularly preferably from 40 to 50 parts by volume.

The water of reaction formed during the course of the reaction (in each case one mol per mole of alcohol group, aldehyde group or keto group reacted) generally does not have an adverse effect on the degree of conversion, the reaction rate, the selectivity and the catalyst operating life and is therefore advantageously removed from the reaction product, e.g. by distillation, only during the work-up of the reaction product.

Excess hydrogen and any excess aminating agent present are removed from the reaction output, advantageously after the latter has been depressurized, and the crude reaction product obtained is purified, e.g. by fractional rectification. Suitable work-up methods are described, for example, in EP 1 312 600 A and EP 1 312 599 A (both BASF AG). The excess aminating agent and the hydrogen are advantageously recirculated to the reaction zone. The same applies to any incompletely reacted alcohol, aldehyde or ketone component.

Unreacted starting materials and any suitable by-products obtained can be recirculated to the synthesis. Unreacted starting materials can, after condensation of the products in the separator, again be passed discontinuously or continuously in the recycle gas stream over the catalyst bed.

The process of the invention can in principle be used to prepare all amines known to those skilled in the art. This applies correspondingly to the starting materials used in the production process. As starting materials, use is made of a nitrogen-comprising compound (N) as aminating agent and also a compound to be aminated, e.g. a primary alcohol or an aldehyde. Furthermore, hydrogen is generally used as starting material. Suitable starting materials and the product (amine (A)) formed in this process are disclosed, for example, in WO 2011/067199.

The process of the invention for preparing an amine (A) is preferably carried out by reacting a primary alcohol, a secondary alcohol, an aldehyde and/or a ketone with hydrogen and a nitrogen-comprising compound (N). The nitrogen-comprising compound (N) is preferably ammonia, a primary amine and/or a secondary amine. Further preference is given to the primary alcohol, the secondary alcohol, the aldehyde, the ketone and/or the nitrogen-comprising compound (N) being used as aqueous solution.

Suitable alcohols are, subject to the abovementioned prerequisites, virtually all primary and secondary alcohols having an aliphatic OH function. The alcohols can be linear, branched or cyclic. Secondary alcohols are aminated the same as primary alcohols. The alcohols can additionally bear substituents or comprise functional groups which are inert under the conditions of the hydrogenative amination, for example alkoxy, alkenyloxy, alkylamino or dialkylamino groups, or can optionally also be hydrogenated under the conditions of the hydrogenative amination, for example CC double or triple bonds. If polyhydric alcohols, e.g. diols or triols, in particular glycols, are to be aminated, amino alcohols, cyclic amines or multiply aminated products can be obtained preferentially by controlling the reaction conditions.

The amination of 1,2-diols leads, depending on the choice of reaction conditions, especially to 1-amino-2-hydroxy or 1,2-diamino compounds.

The amination of 1,4-diols leads, depending on the choice of reaction conditions, to 1-amino-4-hydroxy, 1,4-diamino compounds or to five-membered rings having a nitrogen atom (pyrrolidines).

The amination of 1,6-diols leads, depending on the choice of reaction conditions, to 1-15 amino-6-hydroxy, 1,6-diamino compounds or to seven-membered rings having a nitrogen atom (hexamethylenimines).

The amination of 1,5-diols leads, depending on the choice of reaction conditions, to 1-amino-5-hydroxy, 1,5-diamino compounds or to six-membered rings having a nitrogen atom (piperidines, 1,5-dipiperidinylpentanes).

Accordingly, amination of diglycol (DEG) by means of $NH_3$ can give monoaminodiglycol (=ADG=$H_2N$—$CH_2CH_2$—O—$CH_2CH_2$—OH), diaminodiglycol ($H_2N$—$CH_2CH_2$—O—$CH_2CH_2$—$NH_2$) or morpholine. Particular preference is given here to ADG as process product.

Correspondingly, piperazine is particularly preferably obtained from diethanolamine. N-(2-Hydroxyethyl)piperazine can be obtained from triethanolamine.

Particularly preferred alcohols are methanol, ethanol, n-propanol, i-propanol, n-butanol, sec-butanol, 1,4-butanediol, 1,5-pentanediol, 1,6-hexanediol, 2-ethylhexanol, cyclohexanol, fatty alcohols, ethylene glycol, diethylene glycol (DEG), triethylene glycol (TEG), 2-(2-dimethylaminoethoxyl)ethanol, N-methyldiethanolamine and 2-(2-dimethylaminoethoxy)ethanol.

Ketones suitable for use in the process of the invention are, subject to the abovementioned prerequisites, virtually all aliphatic and aromatic ketones. The aliphatic ketones can be linear, branched or cyclic and can comprise heteroatoms. The ketones can also bear substituents or comprise functional groups which are inert under the conditions of the hydrogenative amination, for example alkoxy, alkenyloxy, alkylamino or dialkylamino groups, or may also optionally be hydrogenated under the conditions of the hydrogenative amination, for example CC double or triple bonds. If a plurality of ketones are aminated, amino ketones, amino alcohols, cyclic amines or multiply aminated products can be obtained by controlling the reaction conditions.

The following ketones are preferably aminatively hydrogenated:

acetone, ethyl methyl ketone, methyl vinyl ketone, isobutyl methyl ketone, butanone, 3-methylbutan-2-one, diethyl ketone, tetraione, acetophenone, p-methylacetophenone, p-methoxyacetophenone, m-methoxyacetophenone, 1-acetylnaphthalene, 2-acetylnaphthalene, 1-phenyl-3-butanone, cyclobutanone, cyclopentanone, cyclopentenone, cyclohexanone, cyclohexenone, 2,6-dimethylcyclohexanone, cycloheptanone, cyclododecanone, acetylacetone, methylglyoxal and benzophenone.

Aldehydes suitable for use in the process of the invention are, subject to the abovementioned prerequisites, virtually all aliphatic and aromatic aldehydes. The aliphatic aldehydes can be linear, branched or cyclic and can comprise heteroatoms. The aldehydes can also bear substituents or comprise functional groups which are inert under the conditions of the hydrogenative amination, for example alkoxy, alkenyloxy, alkylamino or dialkylamino groups, or may optionally also be hydrogenated under the conditions of the hydrogenative amination, for example CC double or triple bonds. If a plurality of aldehydes or ketoaldehydes are aminated, amino alcohols, cyclic amines or multiply aminated products can be obtained by controlling the reaction conditions.

The following aldehydes are preferably aminatively hydrogenated:

formaldehyde, acetaldehyde, propionaldehyde, n-butyraldehyde, isobutyraldehyde, pivalaldehyde, n-pentanal, n-hexanal, 2-ethylhexanal, 2-methylpentanal, 3-methylpentanal, 4-methylpentanal, glyoxal, benzaldehyde, p-methoxybenzaldehyde, p-methylbenzaldehyde, phenylacetaldehyde, (p-methoxyphenyl)acetaldehyde, (3,4-dimethoxyphenyl)acetaldehyde, 4-formyltetrahydropyran, 3-formyltetrahydrofuran, 5-formylvaleronitrile, citronellal, lysmeral, acrolein, methacrolein, ethylacrolein, citral, crotonaldehyde, 3-methoxypropionaldehyde, 3-aminopropionaldehyde, hydroxypivalaldehyde, dimethylolpropionaldehyde, dimethylolbutyraldehyde, furfural, glyoxal, glutaraldehyde and hydroformylated oligomers and polymers, e.g. hydroformylated polyisobutene (polyisobutenealdehyde) or the oligomer obtained by metathesis of 1-pentene and cyclopentene and hydroformylation.

When ammonia is used as aminating agent, the alcoholic hydroxyl group or the aldehyde group or the keto group is firstly converted into the primary amino group (—NH$_2$). The primary amine formed in this way can react with further alcohol or aldehyde or ketone to form the corresponding secondary amine and this can in turn react with further alcohol or aldehyde or ketone to form the corresponding, preferably symmetrical, tertiary amine. Depending on the composition of the reaction mixture or the feed stream (in the case of a continuous mode of operation) and depending on the reaction conditions, viz. pressure, temperature, reaction time (space velocity over the catalyst), employed, primary, secondary or tertiary amines can be prepared preferentially as desired in this way.

Amines which are particularly preferably prepared by the process of the invention are, for example, morpholine (from monoaminodiglycol), monoaminodiglycol, morpholine and/or bis(2-morpholinoethyl) ether (DMDEE) (from DEG and ammonia), 6-dimethyl-amino-1-hexanol (from hexanediol and dimethylamine (DMA)), triethylamine (from ethanol and diethylamine (DEA)), dimethylethylamine (from ethanol and DMA), N—(C$_{1-4}$-alkyl)morpholine (from DEG and mono (C$_{1-4}$-alkyl)amine), N—(C$_{1-4}$-alkyl)piperidine (from 1,5-pentanediol and mono(C$_{1-4}$-alkyl)amine), piperazine and/or diethylenetriamine (DETA) (from N-(2-aminoethyl)ethanolamine (AEEA) and ammonia), N-methyl-piperazine (from diethanolamine and MMA), N,N'-dimethylpiperazine (from N-methyldiethanolamine and MMA), 1,2-ethylenediamine (EDA) and/or diethylenetriamine (DETA) and/or PIP (from monoethanolamine (MEOA) and ammonia), 2-ethylhexylamine and bis(2-ethylhexyl)amine (from 2-ethylhexanol and NH$_3$), tridecylamine and bis(tridecyl)amine (from tridecanol and NH$_3$), n-octylamine (from n-octanol and NH$_3$), 1,2-propylenediamine (from 2-hydroxypropylamine and NH$_3$), 1-diethylamino-4-aminopentane (from 1-diethylamino-4-hydroxypentane and NH$_3$), N,N-di(C$_{1-4}$-alkyl) cyclohexylamine (from cyclohexanone and/or cyclohexanol and di(C$_{1-4}$-alkyl)amine), e.g. N,N-dimethyl-N-cyclohexylamine (DMCHA), polyisobutenamine (PIBA; where, for example, n~1000) (from polyisobutenealdehyde and NH$_3$), N,N-diisopropyl-N-ethylamine (Hünig base) (from N,N-diisopropylamine and acetaldehyde), N-methyl-N-isopropylamine (MMIPA) (from monomethylamine and acetone), n-propylamines (e.g. mono-/di-n-propylamine, N,N-dimethyl-N-n-propylamine (DMPA)) (from propionaldehyde and/or n-propanol and NH$_3$ or DMA), N,N-dimethyl-N-isopropylamine (DMIPA) (from i-propanol and/or acetone and DMA), N,N-dimethyl-N-butylamines (1-butanol, 2-butanol or isobutanol and/or butanal, i-butanal or butanone and DMA), 2-(2-di(C$_{1-4}$-alkyl)aminoethoxy)ethanol and/or bis (2-di(C$_{1-4}$-alkyl)aminoethyl) ether (from DEG and di(C$_{1-4}$-alkyl)amine), 1,2-ethylenediamine (EDA), monoethanolamine (MEOA), diethylenetriamine (DETA) and/or piperazine (PIP) (from monoethylene glycol (MEG) and ammonia), 1,8-diamino-3,6-dioxaoctane and/or 1-amino-8-hydroxy-3,6-dioxaoctane (from triethylene glycol (TEG) and ammonia), 1-methoxy-2-propylamine (1-methoxyisopropylamine, MOIPA) (from 1-methoxy-2-propanol and ammonia), N-cyclododecyl-2,6-dimethylmorpholine (dodemorph) (from cyclododecanone and/or cyclododecanol and 2,6-dimethylmorpholine), polyetheramine (from the corresponding polyether alcohol and ammonia). The polyether alcohols are, for example, polyethylene glycols or polypropylene glycols having a molecular weight in the range from 200 to 5000 g/mol; the corresponding polyetheramines can be obtained, for example, under the trade names PEA D230, D400, D2000, 1403 or T5000 from BASF.

The amine (A) is particularly preferably at least one amine selected from among monoaminodiglycol (ADG), morpholine, N—(C$_{1-4}$-alkyl)morpholine, 2-(2-di(C$_{1-4}$-alkyl)-aminoethoxy)ethanol, bis(2-di(C$_{1-4}$-alkyl)aminoethyl) ether, monoethanolamine (MEOA), 1,2-ethylenediamine (EDA), polyetheramines, piperazine, diethylenetriamine (DETA) and polyisobutenamine (PIBA).

In a preferred embodiment of the present invention, monoaminodiglycol (ADG) and morpholine are prepared by reacting diethylene glycol (DEG) with ammonia.

In a further preferred embodiment of the present invention, N—(C$_{1-4}$-alkyl)morpholine is prepared by reacting diethylene glycol (DEG) with mono(C$_{1-4}$-alkyl)amine.

In a further preferred embodiment of the present invention, 2-(2-di(C$_{1-4}$-alkyl)-aminoethoxy)ethanol and/or bis(2-di(C$_{1-4}$-alkyl)aminoethyl) ether are prepared by reacting diethylene glycol (DEG) with di(C$_{1-4}$-alkyl)amine.

In a further preferred embodiment of the present invention, monoethanolamine (MEOA) and/or 1,2-ethylenediamine (EDA) are prepared by reacting monoethylene glycol (MEG) with ammonia.

In a further prepared embodiment of the present invention, 1,2-ethylenediamine (EDA) is prepared by reacting monoethanolamine (MEOA) with ammonia.

In a further preferred embodiment of the present invention, a polyetheramine is prepared by reacting a corresponding polyether alcohol with ammonia.

In a further preferred embodiment of the present invention, piperazine and/or diethylenetriamine (DETA) are prepared by reacting N-(2-aminoethyl)ethanolamine (AEEA) with ammonia.

In a further preferred embodiment of the present invention, polyisobutenamine (PIBA) is prepared by reacting polyisobutenealdehyde with ammonia.

The invention is illustrated below with the aid of examples.

EXAMPLES

A) Production of the Solutions

A1) Metal salt solution (MSS1)

8.2 kg of nickel nitrate solution (13.5% Ni content), 3.9 kg of copper nitrate solution (15.5% Cu content) and 9.0 kg of cobalt nitrate solution (12.2% Co content) are combined to form solution (MSS1) and stored at room temperature (RT). The solution (MSS1) is stable and remains clear for days at room temperature.

A2) Sn Solution, Cold (SnS1)

3.3 kg of 65% strength nitric acid are diluted to about 30% by addition of 4 kg of ice and cooled to about −15° C. during this dissolution process. 100 g of tin powder are added, and after dissolution has occurred the temperature of the solution is about −5° C. The solution (SnS1) is thermostated at 0° C. and under these conditions remains stable and clear for at least one day.

A3) Sn Solution with Citric Acid (SnS2)

354 g of citric acid are added to a further batch of the solution (SnS1) after dissolution of the tin. After warming of the solution to room temperature, the solution (SnS2) remains stable and clear for days.

A4) Sn Solution with Citric Acid and Metal Salt (SnS3)

Solution (SnS2) at room temperature and solution (MSS1) are combined. The solution (SnS3) remains stable and clear for days.

A5) Sn Solution with Metal Salt at 0° C. (SnS4)

A further batch of the solution (MSS1) is cooled by means of a cryostat to 0° C. and combined at 0° C. with a further batch of the solution (SnS1). The solution (SnS4) remains stable and clear for at least one day at 0° C.

A6) Sn Solution with Metal Salt at RT (SnS5)

Further batches of solution (SnS1) (at 0° C.) and solution (MSS1) (at room temperature) are combined to form solution (SnS5). After about one hour without active cooling, turbidity and commencement of precipitation can be observed. According to analysis, this is due to an Sn-comprising solid.

A7) Sn Solution with Metal Salt and Citric Acid (SnS6)

354 g of citric acid are added at room temperature to 7.3 kg of 30% strength nitric acid. 100 g of tin powder are subsequently added at room temperature. The tin powder dissolves within a few minutes; the resulting solution remains stable and clear for days at room temperature. After the stability check, this solution is combined at room temperature with a further batch of the solution (MSS1) to give the solution (SnS6) which in turn remains stable and clear for days at room temperature.

B) Production of the Catalysts

B1) Catalyst Comprising 17.6% of Ni, 17.3% of Co, 9.7% of Cu, 0.9% of Sn, Balance $Al_2O_3$ (Comparison)

An aqueous solution of nickel nitrate, cobalt nitrate, copper nitrate, tin chloride and finely dispersed aluminum oxide powder (D10-10 from BASF SE), which on a calculated basis comprises 1.96% by weight of each of NiO and CoO, 0.94% of CuO, 0.09% of SnO and 3.76% of $Al_2O_3$, is precipitated simultaneously in a constant stream with a 20% strength by weight aqueous sodium carbonate solution at a temperature of 70° C. in a stirred vessel in such a way that the pH measured by means of a glass electrode was maintained at 7.0. The suspension obtained is filtered and the filter cake is washed with deionized water until the electrical conductivity of the filtrate is about 20 µS. The filter cake is then dried at a temperature of 150° C. in a drying oven or a spray dryer. The hydroxide-carbonate mixture obtained in this way is then calcined at a temperature of from 450 to 500° C. for a period of four hours. The catalyst produced in this way has the composition: 23% by weight of each of NiO and CoO, 11% of CuO, 1% of SnO and 42% of $Al_2O_3$.

The catalyst is mixed with 3% by weight of graphite and shaped to give pellets. The oxidic pellets are reduced. The reduction is carried out at 280° C., with the heating rate being 3° C./minute. The reduction is firstly carried out for 50 minutes using 10% of $H_2$ in $N_2$, then for 10 minutes using 75% of $H_2$ in $N_2$ and finally for 3 hours using 100% of $H_2$. The percentages indicated are percent by volume. The passivation of the reduced catalyst is carried out at room temperature in diluted air (air in $N_2$ having an $O_2$ content of not more than 5% by volume).

In addition, the chlorine content is determined and found to be 0.09%.

B2) Catalyst Based on Solution (SnS5)/(Comparison)

The complete solution (SnS5) from example A6 and aqueous 20% strength sodium carbonate solution are simultaneously added at a temperature of 65-70° C. to a suspension of 2.4 kg of $Al_2O_3$ (D10-10 from BASF, loss on ignition 12%) in 7.5 kg of $H_2O$ in such a way that a pH measured by means of a glass electrode of 5.7+/−0.1 is maintained. After the precipitation, air is blown in for one hour in order to remove dissolved $CO_2$, and the pH of the suspension is then set to 7.4 by means of 20% strength sodium carbonate solution. The suspension obtained is filtered and the filter cake is washed with deionized water until the electrical conductivity of the filtrate is about 500 microS. The filter cake is then dried at a temperature of 120° C. The hydroxide-carbonate mixture obtained in this way is then calcined at a temperature of 450° C. for 6 hours in a rotary bulb furnace while passing 200 l/h of air/kg of powder through it. The calcined powder is subsequently mixed with 3% of graphite and shaped to give 3*3 mm pellets having a tapped density of 1300 g/l+/−100 g/l. The pellets obtained in this way are reduced at a temperature of 280-300° C. in a nitrogen/hydrogen mixture (from 1% of $H_2$ in $N_2$ at the beginning up to 50% of $H_2$ in $N_2$). The passivation of the reduced catalyst is subsequently carried out at not more than 35° C. in diluted air (air in $N_2$ having an $O_2$ content of initially 0.1% up to a maximum of 10% by volume). The catalyst obtained in this way has a composition as follows: 18.8% of Ni, 19.2% of Co, 10.6% of Cu, 1.8% of Sn, balance $Al_2O_3$. The catalyst does not comprise any chlorine.

B3) Catalyst Based on Solution (SnS6)

The procedure described in B2 is repeated using the complete solution (SnS6) from example A7. The catalyst obtained in this way has a composition as follows: 18.0% of Ni, 18.5% of Co, 10.1% of Cu, 1.7% of Sn, balance $Al_2O_3$. The catalyst does not comprise any chlorine.

C) Catalysis Tests in a Continuously Operated Monoline Reactor

A heated tube reactor comprising four tubes which are connected in series and each have a length of 2.5 m and an internal diameter of 4 mm is charged with about 80 g of one of the above-described catalysts; the lower and upper parts of each tube (in each case about 10-20% of the tube volume) are filled with a layer of glass spheres.

Before the reaction, the catalyst is activated at 280° C. while passing 20 standard l/h of hydrogen through it at atmospheric pressure for 24 hours. After reducing the temperature to about 200° C. and increasing the pressure to 200 bar, diethylene glycol (1.0 kg/l/h), ammonia (molar ratio of $NH_3$:DEG=6) and hydrogen (molar ratio of $H_2$:DEG=0.8) are passed through the reactor from the bottom upward. The reaction temperature is subsequently set so that a DEG conversion of about 70% is achieved. The mixture leaving the reactor is cooled and depressurized to atmospheric pressure. After a running-in phase of about 500 hours, samples of the reaction mixture (liquid output) are taken and analyzed by gas chromatography. The results are shown in the table below. The values for the amine selectivity reported in table 1 below are based on the sum of the two reaction products monoaminodiglycol (ADG) and morpholine obtained.

TABLE 1

| Example | Catalyst | Temperature | DEG conversion mol % | Amine selectivity mol % |
|---|---|---|---|---|
| C1 | B1-comparison | 205 | 69 | 91 |
| C2 | B2-comparison | 203 | 70 | 90 |
| C3 | B3-according to the invention | 205 | 69 | 92 |

After removal of the comparative catalyst C1 from the reactor, the chlorine content is determined again; a reduction from 0.09% to 0.01% is observed.

The example according to the invention (C3) clearly shows that the stabilization of the Sn solution makes it possible to obtain a selectivity increased by 1-2% points at virtually unchanged activity compared to catalysts which are produced according to the prior art (C1) or for which an unstable Sn solution is used (C2). In addition, the catalysts according to the invention do not comprise any chlorine which is lost during the course of the reaction (see example C1) and thus leads to corrosion problems.

The invention claimed is:
1. A supported tin-comprising catalyst which is produced by a process wherein a solution (S) comprising tin nitrate and at least one complexing agent is applied to the support, where the solution (S) does not comprise any solid or comprises a solids content of not more than 0.5% by weight based on the total amount of dissolved components, wherein the catalyst comprises
   i) from 0.2 to 5% by weight of tin,
   ii) from 15 to 80% by weight of aluminum,
   iii) from 1 to 20% by weight of copper,
   iv) from 5 to 35% by weight of nickel and
   v) from 5 to 35% by weight of cobalt,
   where the proportions by weight of the components i) to v) are determined as oxides after a calcination step and before a reduction step using hydrogen.
2. The catalyst according to claim 1, wherein the catalyst does not comprise any chlorine.
3. A process comprising preparing an amine (A) in the presence of the catalyst according to claim 1.
4. The process according to claim 3, wherein a primary alcohol, a secondary alcohol, an aldehyde or a ketone is reacted with hydrogen and a nitrogen-comprising compound (N).
5. The process according to claim 4, wherein the nitrogen-comprising compound (N) is ammonia, a primary amine or a secondary amine.
6. The process according to claim 3, wherein the primary alcohol, the secondary alcohol, the aldehyde, the ketone or the nitrogen-comprising compound (N) is used as aqueous solution.
7. The process according to claim 3, wherein the amine (A) is at least one amine selected from among monoaminodiglycol (ADG), morpholine, N—($C_{1-4}$-alkyl)morpholine, 2-(2-di($C_{1-4}$-alkyl)aminoethoxy)ethanol, bis(2-di($C_{1-4}$-alkyl)aminoethyl) ether, monoethanolamine (MEOA), 1,2-ethylenediamine (EDA), polyetheramines, piperazine, diethylenetriamine (DETA) and polyisobutenamine (PIBA).
8. The process according to claim 3, wherein monoaminodiglycol (ADG) and morpholine are prepared by reacting diethylene glycol (DEG) with ammonia.

* * * * *